United States Patent [19]
van Gelderen

[11] Patent Number: 5,414,478
[45] Date of Patent: May 9, 1995

[54] APPARATUS AND METHOD FOR DETERMINING CONTACT LENSES

[76] Inventor: Herman van Gelderen, Doorniksestraat 4, The Hague, Netherlands, 2587 XL

[21] Appl. No.: 124,855

[22] Filed: Sep. 22, 1993

Related U.S. Application Data

[63] Continuation of Ser. No. 973,433, Nov. 9, 1992, abandoned, which is a continuation of Ser. No. 446,851, Dec. 6, 1989, abandoned.

[51] Int. Cl.$^6$ ................................................ A61B 3/10
[52] U.S. Cl. ..................................... 351/212; 351/205; 351/247
[58] Field of Search ............... 351/205, 211, 212, 247; 606/4, 5, 6; 128/745

[56] References Cited

U.S. PATENT DOCUMENTS 3,290,927 12/1966 Gambs ................................. 351/212
4,796,989 1/1989 Fukuma ................................ 351/212

*Primary Examiner*—William L. Sikes
*Assistant Examiner*—Hung Xuan Dang
*Attorney, Agent, or Firm*—Foley & Lardner

[57] ABSTRACT

Apparatus and method for determining a prescription for contact lenses, comprising in cooperative combination a refractometer and a keratometer, both hooked up to a computer, comprising a program for processing the results obtained from said meters in any desired sequence, optionally supplemented with personal data and the results of a tono-meter and/or vertexmeter in optional sequence. The apparatus and method are also suitable for detecting any requirement for readjustment of the lenses after a period of time of use, comparing the new data with the data stored in the memory of the computer, and providing any readjustment required.

10 Claims, 1 Drawing Sheet

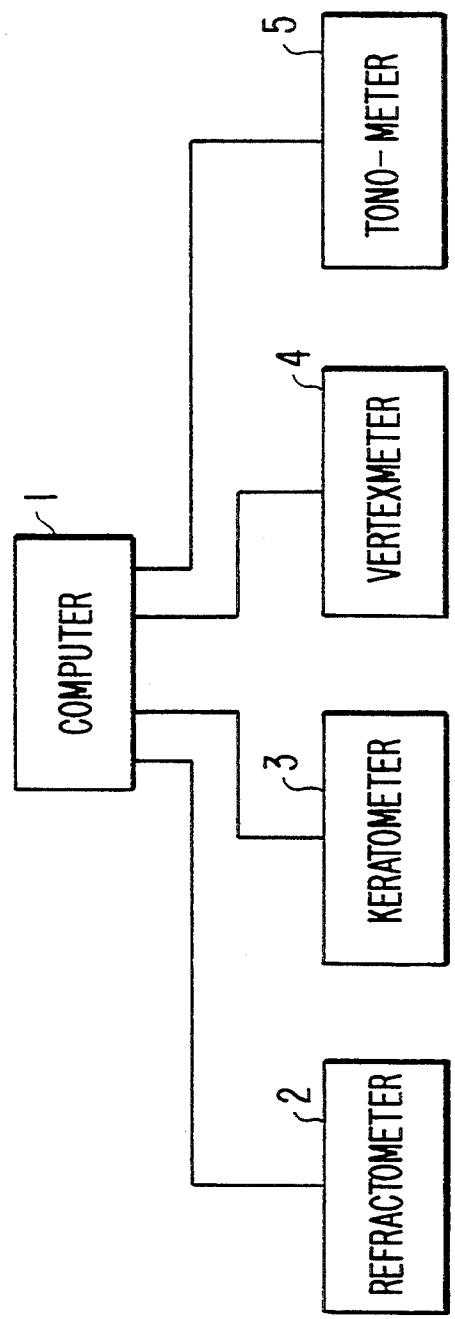

APPARATUS AND METHOD FOR DETERMINING CONTACT LENSES

This application is a continuation of U.S. application Ser. No. 07/973,433, filed Nov. 9, 1992, now abandoned, which is a continuation of U.S. application Ser. No. 07/446,851, filed Dec. 6, 1989, now abandoned.

The invention relates to an apparatus and method for determining a prescription for contact lenses. Both soft and hard lenses are known, which may optionally be permeable. However, it was hitherto not possible to determine the appropriate lens accurately by individuals without expertise in the field of measuring and calculating prescription for lenses. The present invention provides a solution to this problem.

For determining a prescription contact lenses the present invention provides an apparatus and method wherein individuals without special education other than operating the relevant apparatus, are able to determine the appropriate prescription contact lenses. In determining the prescription for a lens, in the present case a contact lens, a considerable number of special circumstances may play a part in determining the appropriate lens to be used. In that respect it can be mentioned by way of example the history of the eye involved, including possible eye-operations, the possibility of allergies, any use of medicines, special conditions in the workplace, such as fumes, air-conditioning, chemicals and smoking, and any medical indication which might prohibit the use of contact lenses. The environmental conditions are of special importance for gas-permeable lenses. In order to collect this information, a list of pertinent questions should be filled out by checking with the client. These data should be stored for determining what type of lens should be used.

The apparatus according to the invention comprises in cooperation a refractometer, a keratometer, a vertexmeter, (a meter for determining the strength of spectacle glasses) and a tono-meter for determining the pressure in an eye-ball. In addition a slit lamp can be used for observation of the lens, conjuctiva and blood vessels in order to obtain possible contra-incications. These measurements can be made automatically or manually. Hitherto the data thus obtained were used for calculation of the prescription for the lens. According to the present invention the data from the instruments used are fed automatically into a computer, wherein the data obtained, together with the special information mentioned in the previous paragraph are combined for obtaining the appropriate details of the lens required.

The customary refractometers, keratometers, vertexmeters and tono-meters for use in the present invention may optionally be provided with a print-out feature for printed out the results of the measurement with the specific meter. Hitherto they have not been used in other than a manual combination, that is, that the results are combined and plugged into a relevant formula. According to the present invention, all meters desired are directly connected with a computer, thus avoiding the need of any expertise of the operator other than handling the apparatus involved. Thus the history of all clients can be entered in a simple manner and without errors, as may occur in manual combination, with the possibility of easy retrieval if required.

In addition, the invention provides a method for determining the appropriate lens for an eye, comprising measuring the eye with a refractometer, a keratometer and optionally a tono-meter, automatically feeding the data of these meters into a computer programmed to plug these data into an appropriate formula, preferably in combination with individual data on history, environmental conditions and medical indication, which may affect the selection of the type of Lens. Thus the client will obtain an accurately calculated lens without any risk of either insufficient expertise or errors in carrying out the calculation, as the programme has been screened accurately.

The apparatus according to the invention not only allows carrying out these measurements, but also takes into account deviations of the eyes such as astigmatism and the like. In addition the apparatus is suitable for taking into account any deviations of the eye resulting from use of the contact lens, such as deformation of the cornea, which may demand switching from spheric lenses to toric, i.e. elliptic lenses and vice versa. Alternatively it may be found that special lenses are required which may be toric or which may require manual manufacture on prescription by an eye-doctor.

The FIGURE shows a schematic representation of a preferred embodiment of the invention.

The invention will now be illustrated by means of the preferred embodiment, without limiting the invention thereto. A questionaire showing up on the computer 1 screen, with only yes or no as alternatives, is checked with the client, with the operator feeding the respective answers to the computer. Subsequently the client is positioned in front of a refractometer 2 which is manipulated by the operator until an optimal result is obtained as indicated by the apparatus. This result is again passed on to the computer. Then the client is positioned in front of a keratometer 3 which is also hooked up to the computer, and again the operator will manipulate the meter until the curvature of the relevant eye is accurately measured, whereupon this result is fed to the computer. If desired the results of similar measurements with a tono-meter 5 and optionally a vertexmeter 4 may be used in any sequence. Subsequently the computer will, on appropriate command, pass on the outcome of the combined information to a printer showing the requirements for the lenses for the eyes concerned. On the basis of that information the lenses can be taken from available shock or be made to measure as the outcome may require.

It will be obvious from the above example that the sequence in which the various operations are carried out is not obligatory and that actually any sequence is suitable, provided that the results of each measurement are passed on to the computer. In addition it should be observed that the basic programme could be complied with by using only the refractometer in combination with the keratometer, thus taking into account the curvature of the eye in determining the ultimate shape of the lens. The vertexmeter is optional for the case where the client is still undecided whether he will opt for lenses or may prefer glasses, or where the history of the client is contra-indicative with respect to the use of lenses.

It should also be observed, that the above apparatus and method allow adjustments of the lenses if required by easy check-up of their effects on the eye, the basic advantage being that under all circumstances individuals without special education in the field can do the job, while simultaneously avoiding human errors as all processing of the results obtained is without human interference.

I claim:

1. An apparatus for prescribing contact lenses, comprising:
   a refractometer for taking a first measurement of a patient's eye and producing a first output signal representative thereof;
   a keratometer for taking a second measurement of the patient's eye and producing a second output signal representative thereof;
   means for inputting personal data of the patient relevant to prescription of contact lenses; and
   processing means for processing said first output signal, said second output signal, and said personal data to prescribe contact lenses.

2. An apparatus for prescribing contact lenses as claimed in claim 1, further comprising a tono-meter for taking a third measurement of the patient's eye and producing a third output signal representative thereof, wherein said processing means processes said third output signal.

3. An apparatus for prescribing contact lenses as claimed in claim 2, further comprising a vertexmeter for taking a fourth measurement of the patient's eye and producing a fourth output signal representative thereof, wherein said processing means processes said fourth output signal.

4. An apparatus for prescribing contact lenses as claimed in claim 1, further comprising a vertexmeter for taking a third measurement of the patient's eye and producing a third output signal representative thereof, wherein said processing means processes said third output signal.

5. A method for prescribing contact lenses using an apparatus comprising a refractometer, a keratometer, and an input device operatively connected to a processing device, comprising the steps of:
   performing a first measurement of a patient's eye using the refractometer;
   performing a second measurement of the patient's eye using the keratometer;
   inputting personal data of the patient relevant to prescription of contact lenses; and
   processing the first measurement, the second measurement, and the personal data with the processing device to determine a prescription for contact lenses.

6. A method for prescribing contact lenses as claimed in claim 5, further comprising the step of performing a third measurement of the patient's eye using a tonometer.

7. A method for prescribing contact lenses as claimed in claim 6, further comprising the step of performing a fourth measurement of the patient's eye using a vertexmeter.

8. A method for prescribing contact lenses as claimed in claim 5, further comprising the step of performing a third measurement of the patient's eye using a vertexmeter.

9. A method for prescribing contact lenses as claimed in claim 5, wherein said personal data includes information concerning the patient's medical history.

10. A method for prescribing contact lenses as claimed in claim 5, wherein said personal data includes information concerning the patient's work environment.

* * * * *